(12) United States Patent  (10) Patent No.: US 8,699,734 B1
Haller  (45) Date of Patent: *Apr. 15, 2014

(54) DUAL MICROPHONE EAS SYSTEM THAT PREVENTS FEEDBACK

(75) Inventor: Matthew I. Haller, Valley Village, CA (US)

(73) Assignee: Advanced Bionics AG, Zug (CH)

( * ) Notice: Subject to any disclaimer, the term of this patent is extended or adjusted under 35 U.S.C. 154(b) by 0 days.

This patent is subject to a terminal disclaimer.

(21) Appl. No.: 13/553,173

(22) Filed: Jul. 19, 2012

Related U.S. Application Data (63) Continuation of application No. 12/584,306, filed on Sep. 3, 2009, now Pat. No. 8,233,651.

(51) Int. Cl.
*H04R 25/00* (2006.01)

(52) U.S. Cl.
USPC .......................................... 381/318; 381/328

(58) Field of Classification Search
USPC ......... 600/25; 607/55, 57; 381/312, 315, 318, 381/328, 330
See application file for complete search history.

(56) References Cited

U.S. PATENT DOCUMENTS

| | | | |
|---|---|---|---|
| 5,343,532 A | 8/1994 | Shugart, III | |
| 5,420,930 A | 5/1995 | Shugart, III | |
| 5,776,179 A * | 7/1998 | Ren et al. | 607/55 |
| 6,342,035 B1 * | 1/2002 | Kroll et al. | 600/25 |
| 6,754,537 B1 | 6/2004 | Harrison et al. | |
| 7,266,208 B2 * | 9/2007 | Charvin et al. | 381/328 |
| 7,561,920 B2 | 7/2009 | Faltys et al. | |
| 7,881,800 B2 | 2/2011 | Daly et al. | |
| 7,995,771 B1 * | 8/2011 | Faltys et al. | 381/328 |

OTHER PUBLICATIONS

Non-Final Office Action received in U.S. Appl. No. 12/584,306 dated Nov. 14, 2011.
Non-Final Office Action received in U.S. Appl. No. 12/553,093 dated Mar. 30, 2012.
Non-Final Office Action received in U.S. Appl. No. 12/584,306 dated Jan. 27, 2012.
Final Office Action received in U.S. Appl. No. 12/553,093 dated Jul. 6, 2012.
Non-Final Office Action received in U.S. Appl. No. 12/553,093, dated Dec. 19, 2012.

* cited by examiner

*Primary Examiner* — Brian Ensey
(74) *Attorney, Agent, or Firm* — ALG Intellectual Property, LLC (57) ABSTRACT

An exemplary method includes an electro-acoustic stimulation (EAS) system associated with a user 1) processing sounds sensed by a first microphone coupled to a cochlear implant portion of the EAS system, 2) applying electrical stimulation representative of the sounds sensed by the first microphone by way of a plurality of electrode contacts located in a basal region of a cochlea of the user, 3) processing sounds sensed by a second microphone coupled to a hearing aid portion of the EAS system, 4) broadcasting, way of a speaker, amplified sound signals representative of the sounds sensed by the second microphone into an ear canal of the user, and 5) acoustically separating the second microphone from the speaker to avoid feedback within the hearing aid portion of the EAS system. Corresponding methods and systems are also disclosed.

17 Claims, 7 Drawing Sheets

FIG. 1

*PRIOR ART*

FIG. 2

*PRIOR ART*

DUAL MICROPHONE EAS SYSTEM THAT PREVENTS FEEDBACK

RELATED APPLICATIONS

The present application is a continuation application of U.S. patent application Ser. No. 12/584,306 by Matthew I. Haller, filed on Sep. 3, 2009, and entitled "Dual Microphone EAS System That Prevents Feedback," which application is incorporated herein by reference in its entirety.

BACKGROUND INFORMATION

The present invention relates to hearing aid systems, and more particularly to a hybrid or Electro Acoustic Stimulation (EAS) hearing aid system that combines a cochlear stimulator and a hearing aid to provide a hearing aid system that relies primarily on the cochlear stimulator portion of the system for being able to sense high frequency sounds, and that relies primarily on normal hearing processes, assisted as required by a hearing aid, for being able to sense lower frequency sounds. A representative hybrid or EAS hearing system is described, e.g., in U.S. Pat. No. 6,754,537, incorporated herein by reference in its entirety.

A hybrid or EAS hearing aid system, such as is disclosed in U.S. Pat. No. 6,754,537, is best suited for use with a short cochlear electrode array of the type described in U.S. Pat. No. 6,889,094 entitled "Electrode Array for Hybrid Cochlear Stimulator", or equivalent short, atraumatic lead. U.S. Pat. No. 6,889,094 is incorporated herein by reference.

A hybrid or EAS cochlear stimulation system provides electrical stimulation only to the basal end of the cochlea to stimulate ganglion cells responsible for sensing higher-frequency sounds, and relies on normal or assisted hearing (activation of hair cells through fluid motion within the cochlea), which may occur with or without the assistance of a conventional or a custom hearing aid, to sense middle-to-lower frequency sounds.

A common problem that plagues hearing aid users is feedback. Feedback occurs in an acoustic amplification system, such as a hearing aid system, when the amplified sound is picked up by the microphone, causing the amplification system to become unstable and squeal. The best way to eliminate feedback is to acoustically separate the microphone from the hearing aid "speaker", or electrical-to-acoustic transducer used to broadcast amplified audio signals against the user's ear drum. However, despite efforts to seal the ear canal (e.g., by preparing an ear mold designed to fit tightly in the ear canal with the microphone held on the side of the mold facing the outside of the ear, and the speaker held on an opposite side of the mold facing the ear drum, with the intent of acoustically separating the speaker from the microphone), some acoustic sound waves broadcast from the speaker always seem to leak back to the microphone, where they are sensed by the microphone, causing the hearing aid system to become unstable and squeal.

Thus, it is seen that there is a need in the art for eliminating feedback in a hearing aid system, and more particularly for eliminating feedback in an EAS hearing prosthesis system utilizing both a cochlear implant for allowing a user to perceive high frequency sound, and a conventional hearing aid for allowing the user to hear low frequency sound.

SUMMARY

The present invention addresses the above and other needs by providing an electro-acoustic stimulation (EAS) system that includes both a hearing aid adapted to sense and amplify low frequency acoustic sound signals and a cochlear implant (CI) adapted to sense high frequency acoustic sound signals. The hearing aid portion of the EAS system has a first microphone adapted to sense low frequency acoustic sound signals, amplify these sensed low frequency acoustic sound signals, and present the resulting amplified low frequency acoustic sound signals in the ear canal of a user, thereby enabling the user to better hear these amplified sounds using his or her normal hearing processes. The cochlear implant portion of the EAS system includes a second microphone adapted to sense the high frequency acoustic sound signals and selectively stimulate the inner ear with electrical stimulation that will be perceived as high frequency acoustic sound signals.

In most instances, both the cochlear implant portion and the hearing aid portion of the EAS system operate on the same ear of the user. For a bilateral EAS system, a respective cochlear implant portion and hearing aid portion could be used in each ear. In some situations, it may be desirable to configure the cochlear implant portion to operate in one ear, and to configure the EAS system to operate in the other ear.

Advantageously, in accordance with the teachings provided herein, feedback within the hearing aid portion of the EAS system is eliminated by positioning the first microphone at a location that is acoustically remote from the ear canal where the amplified low frequency acoustic sound signals are presented. In contrast, high frequency acoustic sound signals are better sensed through the CI portion of the EAS system by placing the second microphone at a location that is in or near the ear canal where the amplified low frequency acoustic sound signals are presented.

It is a feature of the present invention to provide a dual microphone EAS system wherein undesirable feedback is eliminated in the hearing aid portion of the EAS system.

BRIEF DESCRIPTION OF THE DRAWINGS

The above and other aspects, features and advantages of the present invention will be more apparent from the following more particular description thereof, presented in conjunction with the following drawings wherein.

Corresponding reference characters indicate corresponding components throughout the several views of the drawings.

DETAILED DESCRIPTION

The following description is of the best mode presently contemplated for carrying out the invention. This description is not to be taken in a limiting sense, but is made merely for the purpose of describing the general principles of the invention. The scope of the invention should be determined with reference to the claims.

Figure 1:
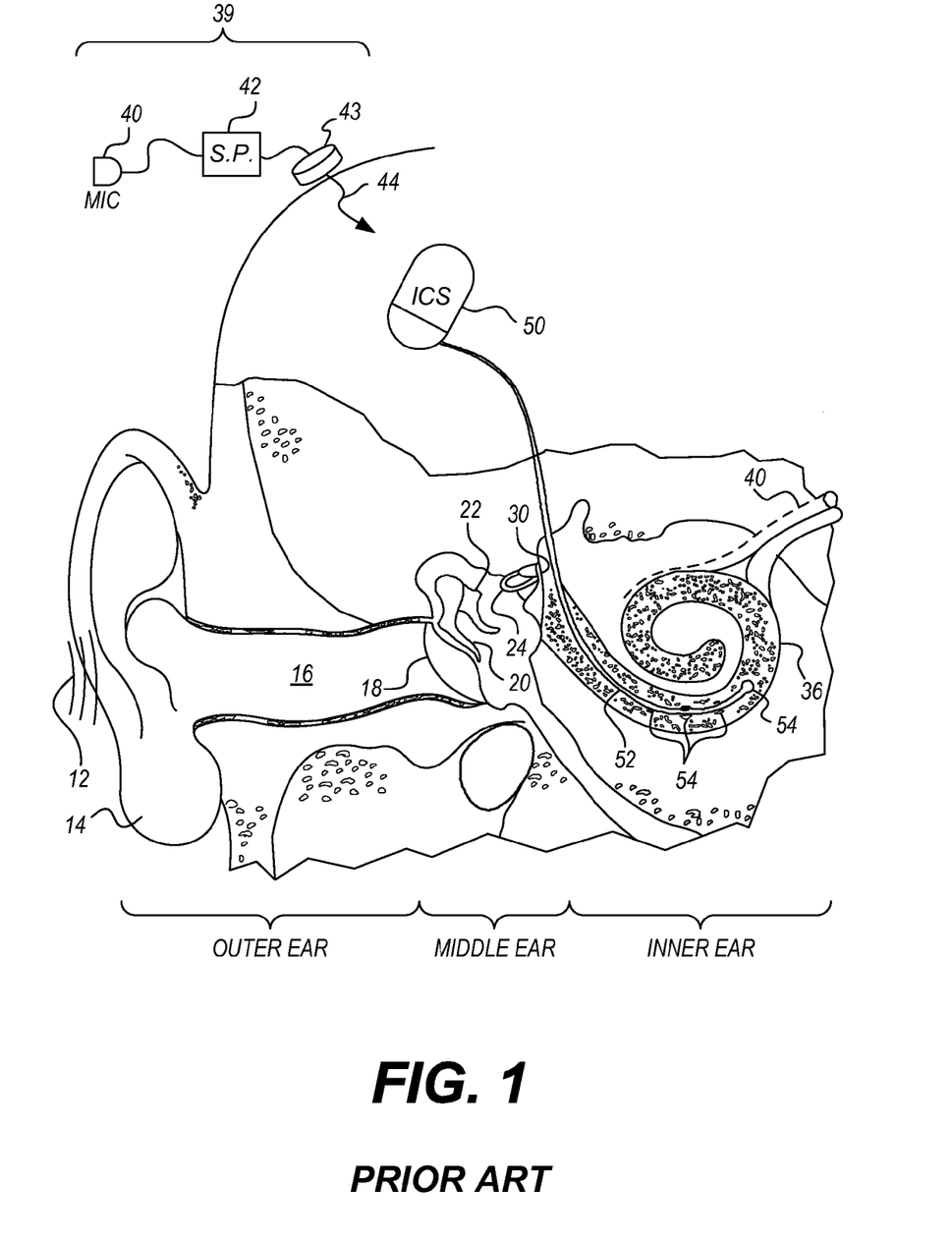
FIG. 1 is a functional schematic diagram of the ear, showing the manner in which an implantable cochlear stimulator and short cochlear electrode array in the basal region of the cochlea may be used to aid a user to better perceive high frequency sound while preserving residual hearing for perceiving low frequency sound.

Turning first to FIG. 1, a system is depicted that uses electrical stimulation of the inner ear to enhance the perception of high frequency sounds, and residual hearing to sense low frequency sounds. The description of this hybrid system (using both electrical stimulation and residual hearing) is presented as background to better understand the operation of the dual microphone EAS system described in more detail below.

As seen in FIG. 1, the major relevant components of the outer, middle and inner ear are illustrated. To better understand the present invention, it will first be helpful to briefly review the normal operation of a fully functional ear. Thus, as seen in FIG. 1, the outer ear includes the auricle 14 and the ear canal 16. An acoustic pressure wave, or sound wave, represented in FIG. 1 by short, spaced-apart, arc lines 12, is collected by the auricle 14 and funneled into the ear canal 16. At the end of the ear cannel 16 is the "ear drum" 18, or in medical terms, the tympanic membrane 18. In a person who is not significantly hearing impaired, the received acoustic wave 12 causes the tympanic membrane 18 to vibrate, which vibration is coupled through three tiny bones, the malleus ("hammer") 20, the incus ("anvil") 22 and the stapes ("stirrup") 24, to the fenestra 30. (In anatomical terms, the fenestra comprises an opening resembling a window. The fenestra ovalis, or oval window, is the opening between the middle ear and the vestibule of the inner ear. It is closed by a membrane to which the stapes is attached. The fenestra rotunda, or round window, is the opening between the scala tympani of the cochlea and the middle ear. The round window is also closed by a membrane, which for purposes of the present application, may be referred to as the basal membrane. For purposes of the schematic diagram shown in FIG. 1, as well as the other figures presented herein, the function of both the oval window and round window is represented by the single membrane 30.)

The bones of the middle ear serve to filter and amplify the perceived acoustic wave 12, causing the fenestra membrane 30 to articulate, or vibrate, in response to the acoustic wave 12. Vibration of the membrane 30 sets up waves of fluid motion within the fluid contained within the snail-shaped cochlea 36. Such fluid motion, in turn, activates tiny hair cells (not shown in FIG. 1) that line the inside of the cochlea 36. Activation of the hair cells causes appropriate nerve impulses to be transferred through the spiral ganglion 40 to the brain, where they are perceived as sound.

The spiral ganglion cells that are responsible for the perception of high frequency sounds are generally located at the basal end of the cochlea 36, i.e., that end of the cochlea closest to the membrane 30. For those individuals who suffer from high frequency hearing loss, the hair cells in the basal region of the cochlea are ineffective or otherwise damaged to the point where it is not possible to activate them with fluid motion within the cochlea. Hence, to overcome this high-frequency hearing deficiency, an implantable cochlear stimulator (ICS) 50 may be implanted near the ear, and a short cochlear electrode array 52, having a plurality of spaced apart electrodes 54 thereon, is inserted into the cochlea 36 through the membrane 30. (In practice, the electrode array 52 may be inserted directly through a slit made in the round window, or it may be inserted through tissue near the round window.).

The ICS 50 is coupled to external components 39, which include a microphone 40, a speech processor 42 and a headpiece 43. Coupling with the ICS may occur through various means, but is usually achieved through an rf and/or electromagnetic coupling link 44 established between an implanted coil located in the ICS, and a coil located in the external head piece 43, connected to the wearable sound processor 42 (or a behind-the-ear (BTE) processor). Such link 44 also provides a way for power to be coupled into the implanted ICS 50. In practice, control signals are typically coupled through the link 44 via radio frequency waves transmitted from an antenna coil in the headpiece 43 to a receiving coil located in the ICS 50. Power is typically coupled through the link 44 via inductive coupling that occurs between the antenna coil located in the headpiece 43 and an implanted coil located in the ICS 50. It is to be noted, that in some embodiments, it is possible for the processor and power source to be implanted, either as an integral part of the ICS 50 or in a separate housing coupled to the ICS. (See, e.g., U.S. Pat. No. 6,272,382 or U.S. Pat. No. 6,308,101, incorporated herein by reference.)

In operation, the speech processor 42 functions as a signal processing means for processing the electrical signals received from the microphone 40 and for generating high frequency control signals therefrom representative of the higher frequency content of the sensed acoustic sounds. These control signals are then coupled to the ICS 50 through the link 44. The ICS 50 has means responsive to the high frequency control signals for selectively generating electrical stimuli and applying the electrical stimuli to the electrode contacts 54 located at or near the distal end of the electrode 52. In this manner, the basal region of the scala tympani duct is stimulated with electrical stimuli representative of the higher frequency content of the sensed acoustic sounds.

In accordance with the configuration depicted in FIG. 1, the sounds sensed by the microphone 40 are processed and filtered to separate out the high frequency sounds. These high frequency sounds are then converted to appropriate electrical stimuli that are selectively applied to the electrode contacts 54 of the electrode array 52 positioned in the basal region of the cochlea. Such electrical stimuli bypass the defective hair cells in the basal region of the cochlea and directly activate the nerves within the of the spiral ganglion, causing nerve impulses to be transferred to the brain, where they may be perceived as high frequency sounds.

The other hair cells in the cochlea, i.e., those in the apical and mid regions of the scala tympani duct, retain their functionality. That is, these hair cells are able to sense the fluid waves set up by vibrations of the membrane 30 corresponding to low-to-mid frequency sounds. Hence, the patient (or user of the hybrid system shown in FIG. 1) is able to sense high frequency sounds through the ICS portion of the system, and is able to sense lower frequency sounds through the normal hearing processes of the ear.

Figure 2:
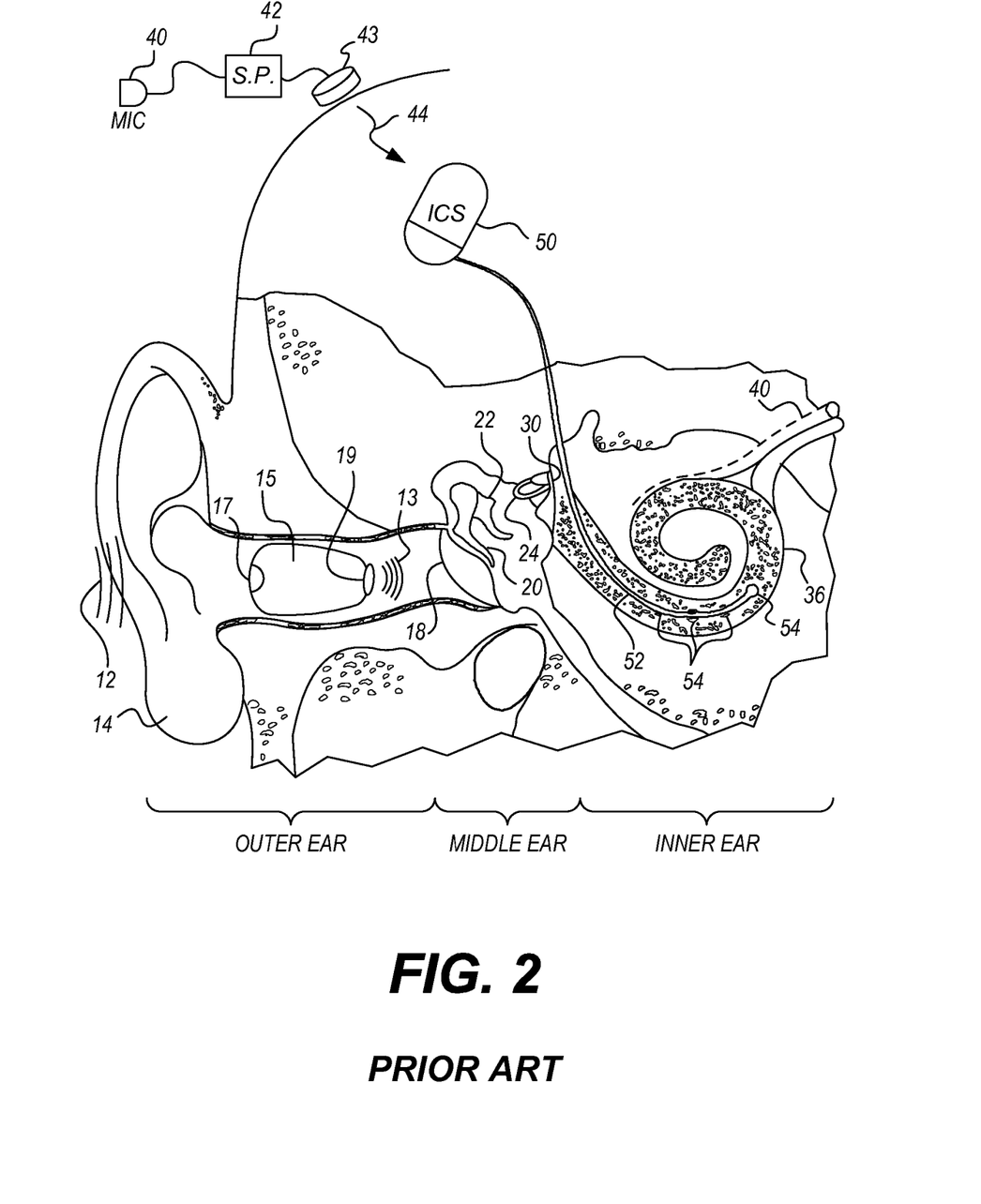
FIG. 2 is a functional schematic diagram of the ear as in FIG. 1, and further shows the manner in which a conventional in-the-ear hearing aid may be used to supplement the manner in which low frequency sounds are perceived.

In FIG. 2, another configuration of an EAS system is depicted. The configuration shown in FIG. 2 is the same as the configuration shown in FIG. 1 except for the addition of an in the canal hearing aid 15. The in the canal hearing aid 15, which may be of conventional design, senses the acoustic waves 12 through a microphone 17, amplifies the signal, and rebroadcasts the signal through an electrical-to-acoustic transducer (or "speaker") 19 as amplified acoustic waves 13. These amplified acoustic waves 13 are directed to the tympanic membrane (or eardrum) 18 located at the end of the ear canal 16. The amplified acoustic waves 13 are thereby able to increase the magnitude of the vibrations that pass through the middle ear and articulate the membrane 30, thereby increasing the magnitude of the fluid waves within the cochlea, which higher magnitude fluid waves may be more effective at activating the hair cells throughout the cochlea. Typically, however, the high frequency hair cells at the basal end of the cochlea remain defective and unresponsive to the higher magnitude fluid waves. Thus, the cochlear stimulator portion (ICS 50 and electrode array 52) of the hybrid system must still be used if high frequency sounds are to be perceived.

Figure 3A:
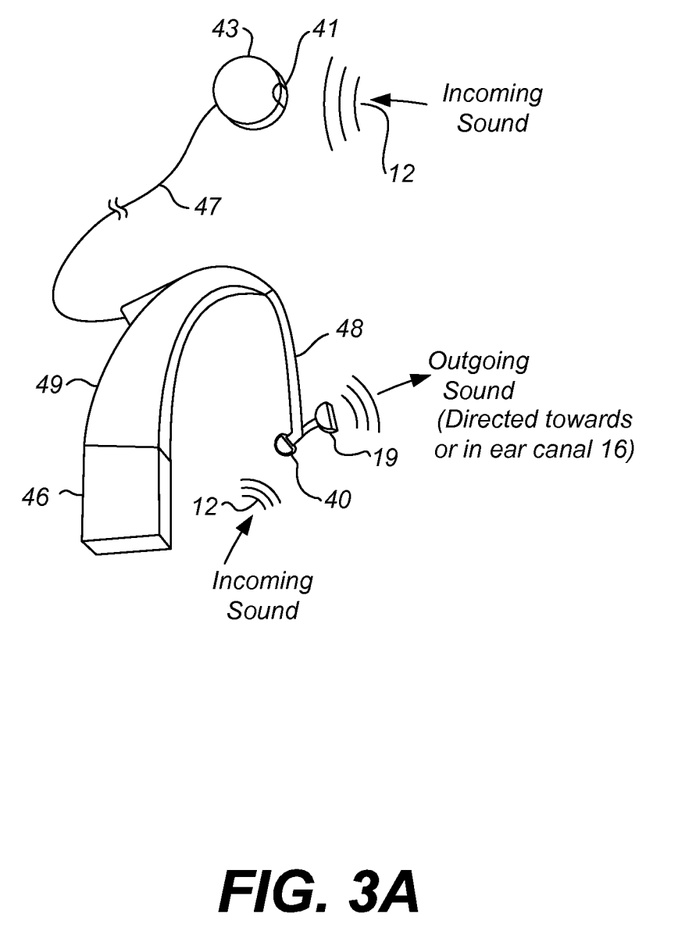
FIG. 3A shows the external components of one preferred embodiment of an EAS system wherein two microphones are used.

Next, with reference to FIG. 3A, the external components of one preferred embodiment of an EAS system are depicted. These external components include a first microphone 40 and a second microphone 41. The first microphone 40 is located at the end of a flexible boom 48 attached to an ear hook of a behind-the-ear (BTE) unit 49. When the BTE unit 49 is placed over the ear, the boom 48 advantageously positions the microphone 40 at a location where sound collected by the auricle 14 (see FIG. 1) is focused, near the opening of the ear canal 16.

Also located near the opening of the ear canal 16 is a speaker 19 that is oriented to direct the sound emitted therefrom towards or in the ear canal 16.

A key feature of the EAS system described herein is that the sounds sensed by the microphone 40 are not the same sounds that are processed and amplified and then emitted from the speaker 19. Rather, the sounds sensed by the microphone 40 are limited to the higher frequency sounds, e.g., sounds associated with frequencies above a frequency $f_H$, where $f_H$ is typically in the range of 800-1000 Hz. These higher frequency sounds are processed by the BTE unit 49, which includes a speech processor 42 as described elsewhere herein.

The speech processor 42 converts the sensed higher-frequency signals to corresponding control signals that are coupled to a cochlear implant (not shown in FIG. 3A, but described in connection with the other figures). The cochlear implant, responsive to these control signals, generates electrical stimulus signals which are selectively applied to electrode contacts 54 of an implantable electrode array 52, as described previously in connection with FIG. 1. These stimulus signals, in turn, activate spiral ganglion cells located near the electrodes, thereby allowing the user to perceive these stimulus signals as the higher-frequency sound which the user otherwise would not be able to perceive.

The second microphone 41 is positioned at a location that is acoustically remote from the speaker 19. One preferred location for the microphone 41 is on the headpiece 43. However, it is to be understood that the microphone 41 may be positioned at other locations as well. The headpiece 43, in turn, is connected to the BTE unit 49 by way of a cable 47. The sounds sensed through the second microphone 41 are limited to the lower and mid-range frequency sounds. Lower frequency sounds, for purposes herein, are sounds having a frequency less than $f_L$, where $f_L$ is typically in the range of 200-400 Hz. Mid-range frequency sounds, for purposes herein, are those sounds having a frequency $f_M$, where $f_M$ is between $f_L$ and $f_H$. These sounds are amplified by a suitable amplifier and/or other sound processing circuits contained with the BTE unit 49 and are presented to the speaker 19 located in or near the opening of the ear canal 16. Because the sounds being emitted by the speaker 19 are different sounds than those sensed by the microphone 40, no undesirable feedback is created. Thus, in this manner, the user is able to perceive and hear both low-to-mid range frequency sounds (as sensed through microphone 41 and amplified and presented to the user through his or her ear canal via speaker 19) as well as high frequency sounds (as sensed through microphone 40 and presented to the user through a cochlear implant system).

The signal processing that takes place in the BTE unit 49 is preferably done using digital circuits that allow a very sharp and precise frequency separation between the low-to-mid range frequency signals that are sensed through microphone 41 and those that are sensed through microphone 40. This prevents undesirable feedback from occurring between the microphone 40 and the speaker 19, which are in close proximity to each other.

Figure 3B:
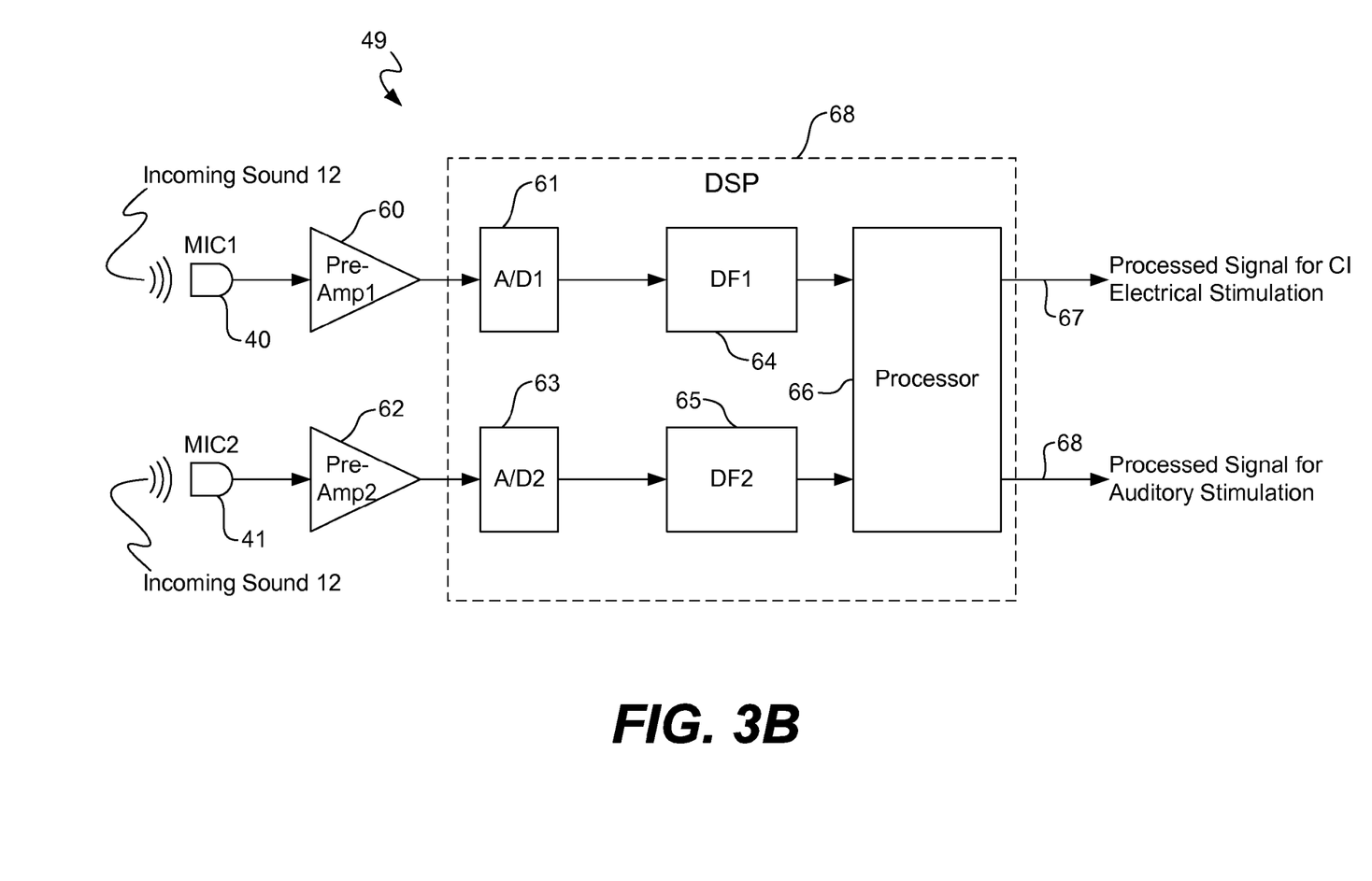
FIG. 3B is a functional block diagram of the sound processing portion of a two microphone EAS system.

Turning next to FIG. 3B, one preferred embodiment of the functional signal processing portions of the EAS system described herein is shown. As seen in FIG. 3B, there are at least two signal processing channels associated with the EAS system. Each channel employs a separate microphone (MIC).

As seen in FIG. 3B, a first microphone 40 (MIC1) is coupled to a first pre-amplifier 60 (Pre-Amp1), the output of which is directed as an input signal to a first analog-to-digital converter 61 (A/D1). The output digital signals from A/D1 are then directed to a first digital filter 64 (DF1), where only the higher frequency signals, i.e., those above frequency $f_H$, are selected for further processing by Processor 66. These higher frequency signals are processed by the Processor 66 and converted to appropriate control signals. These control signals are directed to the cochlear implant (CI) in order to allow the CI to electrically stimulate the appropriate areas of the basal region of the cochlea, thereby allowing the user to better perceive these higher frequency sound signals. As depicted in FIG. 3B, these control signals are functionally directed to the CI over signal line 67.

As further seen in FIG. 3B, a second microphone 41 (MIC2) is coupled to a second pre-amplifier 62 (Pre-Amp2), the output of which is directed as an input signal to a second analog-to-digital converter 63 (A/D2). The output digital signals from A/D2 are then directed to a second digital filter 65 (DF2), where only the mid-to-low frequency signals, i.e., those having a frequency less than $f_H$, are selected for further processing by Processor 66. These mid-to-low frequency signals are processed by the Processor 66 and converted to appropriate output signals. These output signals are functionally directed to a speaker (e.g., speaker 19 shown in FIG. 3A) over signal line 68.

Advantageously, all of the circuits A/D1, A/D2, DF1, DF2, and Processor 66 may be largely digital circuits, and the processing performed thereby may be carried out using programmable digital signal processing (DSP) techniques as are generally known in the art. More significantly, all or most of these circuits may be implemented on the same DSP chip 68, thus making the overall size of the DSP circuits very small.

Moreover, because DSP circuit operation allows, e.g., the cut-off frequencies associated with the DF1 and DF2 digital filters to be precisely set, a sharp separation between the frequencies processed by the first processing channel, comprising MIC1, Pre-Amp1, A/D1, DF1 and a portion of Processor 66, and the second processing channel, comprising MIC2, Pre-Amp2, A/D2, DF2 and a portion of Processor 66, to be defined and maintained. Where this sharp separation occurs will vary from user to user, but will typically be in the 500-2000 Hz range. That is, for some users, any frequencies below a first frequency F1, where F1 may be 500 to 2000 Hz, will be considered as a mid-to-low frequency signal that is processed by the second processing channel; whereas any frequencies above this frequency F1 will be considered a high frequency signal that is processed by the first processing channel.

In some embodiments, it may be advantageous to overlap the frequency cut-off point between where mid-to-low frequency signals end, and the high frequency signals begin. This overlap amount, if used, will generally only be used in one channel, e.g., the CI channel (the first processing channel shown in FIG. 3B), in order to prevent undesirable feedback in the acoustic processing channel (the second processing channel shown in FIG. 3B). That is, for some patients, the CI processing channel, which starts with MIC1, may process all frequency signals (or a large subset of the available frequency signals) present within the incoming sound signal 12 that is sensed by MIC1, and use the information content of these frequency signals to help define the electrical stimuli to be applied to the electrode contacts 54 located at or near the distal end of the electrode 52 inserted into the user's cochlea (as described, e.g., in connection with FIG. 2). However, the acoustic processing channel, which starts with MIC2, will process only those signals within the incoming sound signal 12 that are less than some cut-off frequency F1. The key is that MIC2 be located at a location that is acoustically remote, e.g., on the headpiece 43, from the SPKR 19 (see, e.g., FIGS. 2, 3A and 3C) from which the mid-to-low frequency signals processed by the second processing channel are broadcast.

Figure 3C:
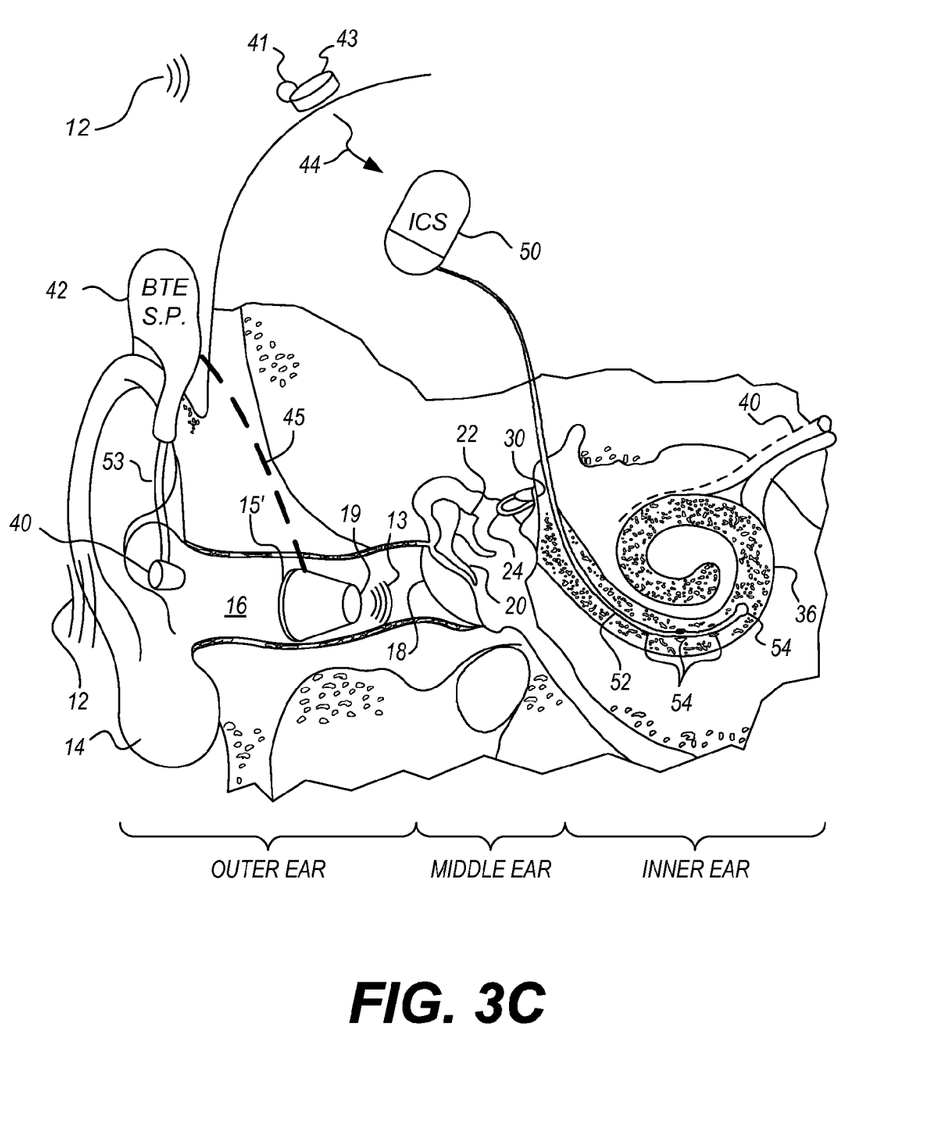
FIG. 3C is a functional schematic diagram of the ear as in FIGS. 1 and 2 and further shows one embodiment of an EAS system wherein two microphones are employed.

Next, with reference to FIG. 3C, a functional schematic diagram of the ear as in FIGS. 1 and 2 is illustrated that further shows one embodiment of an EAS system wherein two microphones are employed. In many respects, the embodiment shown in FIG. 3C is similar to the configuration shown in FIG. 2. However, there are critical differences. Foremost in these differences is the location of the microphone used with the hearing aid portion of the EAS system. In FIG. 2, the microphone 17 is located at a proximal end of the in-the-ear hearing aid 15. This location disadvantageously makes the hearing aid very susceptible to feedback. In FIG. 3C, a microphone 41 used with the hearing aid portion of the EAS system is located at a distance that is acoustically remote from the ear canal 16 or the speaker 19. As shown in FIG. 3C, the microphone 41 is located on or near the headpiece 43 of the ICS portion of the system. Such location is acoustically remote from the ear canal 16 or speaker 19 because the amplified sounds 13 emanating from the speaker (SPKR) 19 cannot be readily perceived at this location. Hence, because of this, no or minimal feedback will occur, and in general, the gain associated with the hearing aid amplifier (which may be located inside the BTE speech processor 42 or within the in-the-canal hearing mold casing 15') can be turned up as loud as necessary.

In one preferred embodiment, the in-the-canal hearing mold 15' shown in FIG. 3C need not be anything more than an ear bud which holds the SPKR 19. In accordance with this embodiment, the amplifier and power circuits and batteries associated with the hearing aid function can be housed in the BTE speech processor 42.

The SPKR 19 is coupled to its amplification and driving circuits via a coupling link 45. In its simplest form, this link 45 may be a pair of wires, conveniently arranged in a single cable, as is commonly done with conventional ear buds connected to audio sources, such as an iPod or cell phone. More sophisticated coupling may occur through other means, such as wireless coupling, as is known in the art. When wireless coupling is used, then at least some amplification circuitry, along with wireless reception circuitry and a power source are housed within the ear canal mold 15' along with the SPKR 19.

Alternatively, the link 45 may be an acoustic link provided, e.g., through an acoustic tube that carries the sound wave signals to the ear drum 18, as is commonly done with many types of hearing aids. In such instance, all of the processing circuits needed to amplify the sound signal are housed, e.g., within the BTE sound processor 42. The acoustic tube may enter the ear canal from the outside, as is conventionally done with most hearing aids, or it can be inserted deep into the ear canal through an auxiliary tunnel, as described, e.g., in U.S. Pat. No. 6,786,860, incorporated herein by reference.

The embodiment shown in FIG. 3C senses acoustic sound waves 12 through either microphone 40, located near the opening of the ear canal 16, or through microphone 41, located at an acoustically remote distance from the ear canal 16. Microphone 40 may be located at the end of a boom 53 connected to an ear hook used with the BTE speech processor 42. See, e.g., U.S. Pat. Nos. 7,106,873 and 7,167,572, incorporated herein by reference.

Figure 4A:
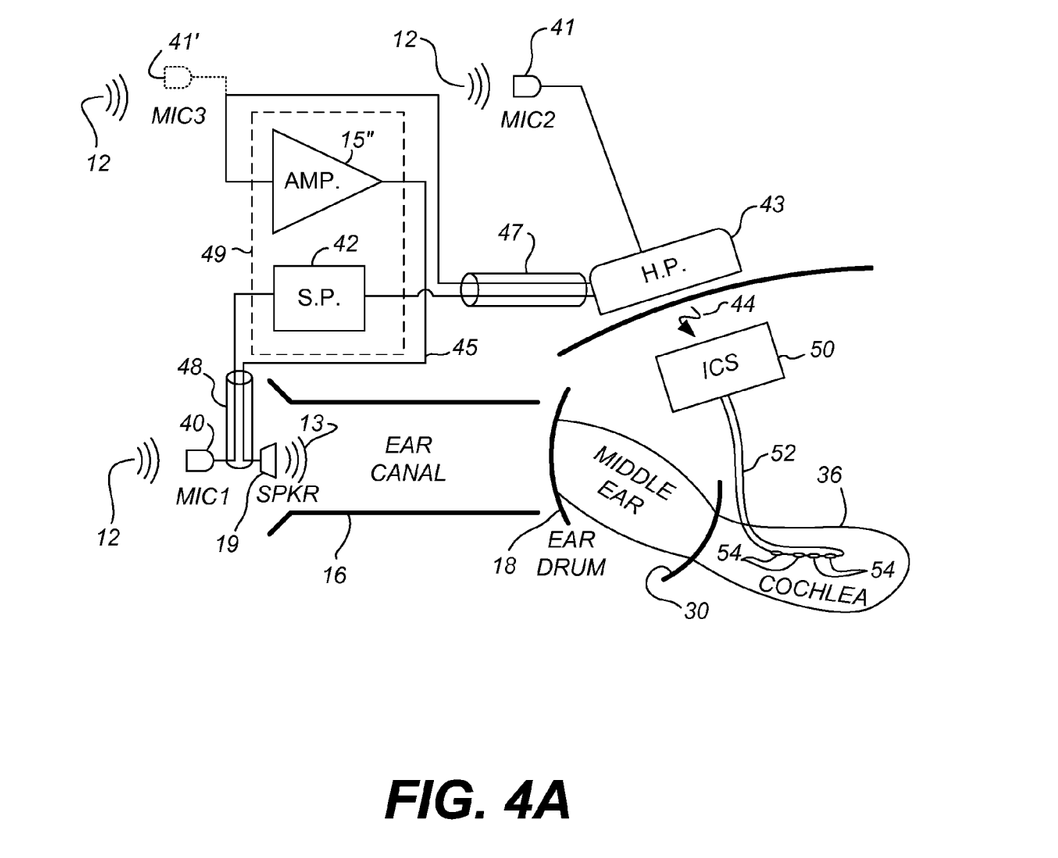
FIG. 4A is a block diagram that depicts an EAS system using multiple microphones, wherein the microphone(s) associated with the hearing aid portion are positioned to eliminate feedback, and further wherein the speaker associated with the hearing aid portion is positioned near the front end of the ear canal.

FIG. 4A shows a functional block diagram of one preferred embodiment of the EAS system described herein. FIG. 4A is very similar to FIG. 3C, except that the physiological components of the ear are shown in a more schematic fashion in FIG. 4A than in FIG. 3C. Also, FIG. 4A illustrates that the microphone 41 used with the hearing aid portion of the EAS system may be located at any location that is acoustically remote from the ear canal 16, not just at a location that is on or near the headpiece 43. That is, FIG. 4A depicts a microphone 41' that may be positioned in any suitable location. Microphone 41 shown in FIG. 3C, in contrast, is shown connected to the headpiece 34, and from there it is coupled through cable 47 to an external housing 49. The external housing 49 may be a BTE housing, or a body-worn housing. The circuitry associated with both the hearing aid amplifier 15" (of the hearing aid portion of the EAS system) and the speech processor 42 (of the ICS portion of the EAS system) may be housed within the housing 49. The output of the amplifier 15" is coupled to the SPKR 19 located in the ear canal 16 by a suitable link 45. As described previously, the link 45 may be of numerous kinds, e.g., wires, wireless, or acoustic. (If an acoustic link is used, the SPKR 19 would actually be located in the housing 49, not in the ear canal 16 as shown in the drawing, and the amplified sound waves 13 would emanate from an acoustic tube, not shown in FIG. 4A, coupled at one end to the SPKR 19, with the other end of the acoustic tube being positioned at a location in or near the ear canal 16 so as to be close to the ear drum 18.)

Figure 4B:
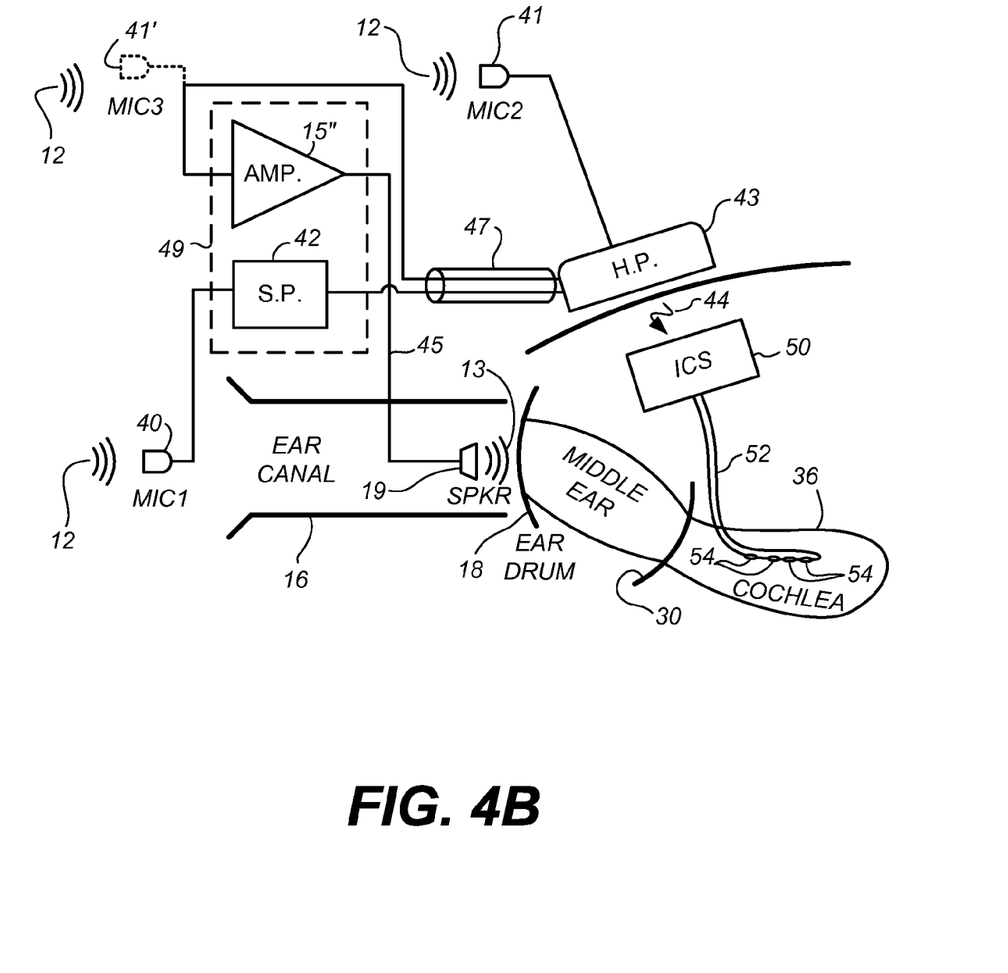
FIG. 4B is a block diagram that depicts an EAS system using multiple microphones, as in FIG. 4A, but wherein the speaker associated with the hearing aid portion is positioned in the ear canal of the user, closer to the ear drum.

FIG. 4B shows a functional block diagram of another preferred embodiment of the EAS system. In most respects, FIG. 4B is the same as FIG. 4A, and the description provided above with respect to FIG. 4A applies equally to FIG. 4B. However, the one main difference between FIG. 4B and FIG. 4A is location of the SPKR 19. In FIG. 4B, the SPKR 19 is placed much closer to the ear drum 18. The link 45 that couples the SPKR 19 to the AMP 15" may again be of numerous kinds, e.g., wires, wireless, or acoustic. If wires are used, the wires may pass through the ear canal, or they may pass through a tunnel made in the soft tissue behind the auricle 14. Placing the SPKR 19 deep into the ear canal 16, as shown in FIG. 4B, serves to further acoustically separate the SPKR 19 from MIC2 (41) or MIC3 (41'), thus preventing feedback.

As described above, it is thus seen that an EAS system is provided that includes both a hearing aid adapted to sense and amplify low frequency acoustic sound signals and a cochlear implant adapted to sense high frequency acoustic sound signals. The hearing aid portion of the EAS system has a first microphone 41 or 41' adapted to sense low frequency acoustic sound signals, amplify these sensed low frequency acoustic sound signals, and present the resulting amplified low frequency acoustic sound signals 13 in the ear canal of a user, thereby enabling the user to better hear these amplified sounds using his or her normal hearing processes. The cochlear implant portion of the EAS system includes a second microphone 40 adapted to sense the acoustic sound signals and selectively stimulate the inner ear with electrical stimulation that will be perceived primarily as high frequency acoustic sound signals. Both the cochlear implant portion and the hearing aid portion of the EAS system are coupled to operate on the same ear of the user.

As further described herein, it is seen that feedback associated within the hearing aid portion of the EAS system is eliminated by positioning the microphone 41 or 41' at a location that is acoustically remote from the ear canal 16 where the amplified low frequency acoustic sound signals are presented. In contrast, high frequency acoustic sound signals are better sensed through the cochlear implant portion of the EAS system by placing the microphone 40 at a location in or near the ear canal 16.

While the invention herein disclosed has been described by means of specific embodiments and applications thereof, numerous modifications and variations could be made thereto by those skilled in the art without departing from the scope of the invention set forth in the claims.

What is claimed is:

1. A method comprising:
processing, by an electro-acoustic stimulation (EAS) system associated with a user, sounds sensed by a first microphone coupled to a cochlear implant portion of the EAS system;
applying, by the EAS system, electrical stimulation representative of the sounds sensed by the first microphone by way of a plurality of electrode contacts located in a basal region of a cochlea of the user;
processing, by the EAS system, sounds sensed by a second microphone coupled to a hearing aid portion of the EAS system;
broadcasting, by the EAS system by way of a speaker, amplified sound signals representative of the sounds sensed by the second microphone into an ear canal of the user; and
acoustically separating, by the EAS system, the second microphone from the speaker to avoid feedback within the hearing aid portion of the EAS system.

2. The method of claim 1, wherein the acoustically separating the second microphone from the speaker comprises placing the second microphone at a location that is acoustically remote from a location of the speaker.

3. The method of claim 2, wherein the speaker is located within the ear canal.

4. The method of claim 1, wherein the cochlear implant portion includes a headpiece adapted to be worn by the user at a location on the user's head that is acoustically remote from the ear canal, and wherein the acoustically separating the second microphone from the speaker comprises placing the second microphone in or on the headpiece.

5. The method of claim 1, further comprising configuring the cochlear implant portion to provide direct electrical stimulation through the electrode contacts only in response to the first microphone sensing high frequency signals.

6. The method of claim 1, further comprising configuring the cochlear implant portion to provide direct electrical stimulation through the electrode contacts only in response to the first microphone sensing sound signals having a frequency $f_H$, where $f_H$ is a frequency value that lies between 800 and 1000 Hz.

7. The method of claim 6, further comprising configuring the hearing aid portion to broadcast sound signals into the ear canal in response to the second microphone sensing low frequency sounds, the low frequency sounds having a frequency no greater than $f_L$, where $f_L$ is a frequency value that lies between 200 and 400 Hz.

8. The method of claim 7, further comprising configuring the hearing aid portion of the EAS system to also broadcast sound signals into the ear canal in response to the second microphone sensing mid-frequency sounds of frequency $f_M$, where $f_M$ is a frequency value greater than $f_L$ and less than $f_H$.

9. A method of applying electro-acoustic stimulation to a patient for the purpose aiding the patient to hear comprising:
electrically stimulating, by an electro-acoustic stimulation (EAS) system associated with a patient, one or more areas of an inner ear of the patient that are responsible for perceiving high frequency sound;
amplifying, by the EAS system, low frequency acoustic signals;
presenting, by the EAS system, the resulting amplified low frequency acoustic signals into the ear canal; and
at least partially eliminating, by the EAS system, feedback of the low frequency acoustic signals;
wherein the low frequency acoustic signals are perceived through normal hearing processes initiated by presenting the amplified low frequency acoustic signals into the ear canal; and
wherein the high frequency acoustic signals are perceived through electrical stimulation presented to the inner ear.

10. The method of claim 9, wherein the electrically stimulating the one or more areas of the inner ear responsible for perceiving high frequency sound comprises:
providing the patient with a cochlear implant system, the cochlear implant system having a first microphone, a sound processor, an implantable pulse generator and a stimulation lead, wherein the stimulation lead has a proximal end connected to the implantable pulse generator and a distal end having at least one electrode;
inserting the distal end of the stimulation lead so that the at least one electrode resides within a basal region of the inner ear;
processing acoustic signals sensed through the first microphone using the sound processor;
generating control signals within the sound processor as a function of the processed acoustic signals and sending the control signals to the implantable pulse generator;
generating stimulation pulses within the implantable pulse generator responsive to the control signals; and
selectively applying the stimulation pulses to the at least one electrode located in the basal region of the inner ear.

11. The method of claim 10, wherein the amplifying of the low frequency acoustic signals and presenting the resulting amplified low frequency signals into the ear canal comprises:
providing the patient with a hearing aid system, the hearing aid system having a second microphone, an amplifier coupled to the second microphone and an amplifier configured to amplify acoustic signals sensed by the second microphone and broadcast the resulting amplified signals into the ear canal;
amplifying only low frequency signals sensed through the second microphone; and
broadcasting the resulting amplified low frequency signals into the ear canal.

12. The method of claim 11, wherein the eliminating of the feedback of the low frequency acoustic signals comprises positioning the second microphone at a location that is acoustically remote from the location where the amplified low frequency signals is broadcast into the ear canal.

13. The method of claim 11, wherein the broadcasting of the resulting amplified low frequency signals into the ear canal comprises positioning a broadcasting output element of the amplifier at a location near the entrance of the ear canal.

14. The method of claim 11, wherein the broadcasting of the resulting low frequency signals into the ear canal comprises positioning a broadcasting output element of the amplifier at a location near the ear drum within the ear canal.

15. The method of claim 11, wherein the cochlear implant system further includes a headpiece adapted to be worn by the patient at a location that is high on the head and behind the ear of the patient, and wherein positioning the second microphone at a location acoustically remote from the location where the amplified low frequency signals is broadcast into the ear canal comprises positioning the second microphone at a location on the headpiece.

16. The method of claim 10, wherein the processing acoustic signals sensed through the first microphone using the sound processor comprises processing acoustic signals having a frequency of at least $f_H$, where $f_H$ is a frequency value that falls within the range of 800 to 1000 Hz.

17. The method of claim 10, wherein the amplifying only low frequency signals sensed through the second microphone comprises amplifying frequencies having a frequency no greater than $f_L$, where $f_L$ is a frequency value that falls within the range of 200 to 400 Hz.

* * * * *